United States Patent [19]
Sanders et al.

[11] Patent Number: 5,895,642
[45] Date of Patent: Apr. 20, 1999

[54] PSEUDOCATALASE ACTIVITY

[75] Inventors: Colin Sanders, Slough; David A. Matkin, Maidenhead; Neale C. Wareham, Aylesbury, all of United Kingdom

[73] Assignee: Stiefel Laboratories, Inc., Coral Gables, Fla.

[21] Appl. No.: 09/051,471

[22] PCT Filed: Nov. 13, 1996

[86] PCT No.: PCT/GB96/02758

§ 371 Date: Apr. 16, 1998

§ 102(e) Date: Apr. 16, 1998

[87] PCT Pub. No.: WO97/17943

PCT Pub. Date: May 22, 1997

[30] Foreign Application Priority Data

Nov. 14, 1995 [GB] United Kingdom ............... 9523249

[51] Int. Cl.$^6$ .................. A61K 7/40; A61K 7/42
[52] U.S. Cl. .................. 424/59; 424/63; 424/401; 424/600; 424/639; 424/641; 424/630; 514/836
[58] Field of Search .................. 424/59, 63, 401, 424/600, 639, 641, 630; 514/836

[56] References Cited

U.S. PATENT DOCUMENTS

| | | |
|---|---|---|
| 5,378,461 | 1/1995 | Neigut . |
| 5,433,942 | 7/1995 | Wood et al. . |
| 5,476,651 | 12/1995 | Meybeck et al. . |
| 5,585,105 | 12/1996 | Junino et al. . |
| 5,587,173 | 12/1996 | Junino et al. . |
| 5,723,109 | 3/1998 | Causse et al. . |

FOREIGN PATENT DOCUMENTS 92-20321  11/1992  WIPO .
92-20354  11/1992  WIPO .

*Primary Examiner*—Carlos A. Azpuru
*Assistant Examiner*—Brian K. Seidleck

[57] ABSTRACT

The in vivo catalytic dismutation of hydrogen peroxide by pseudocatalase such as a transition metal bicarbonate complex is increased by the addition of a chelating agent, preferably ethylenediaminetetraacetic acid (EDTA), citic acid, 2,6-pyridinedicarboxylic acid, or a salt thereof. Further, the stability of a topical composition comprising a transition metal bicarbonate complex is improved by storing the composition under carbon dioxide, preferably under pressure in aerosol form.

20 Claims, 2 Drawing Sheets

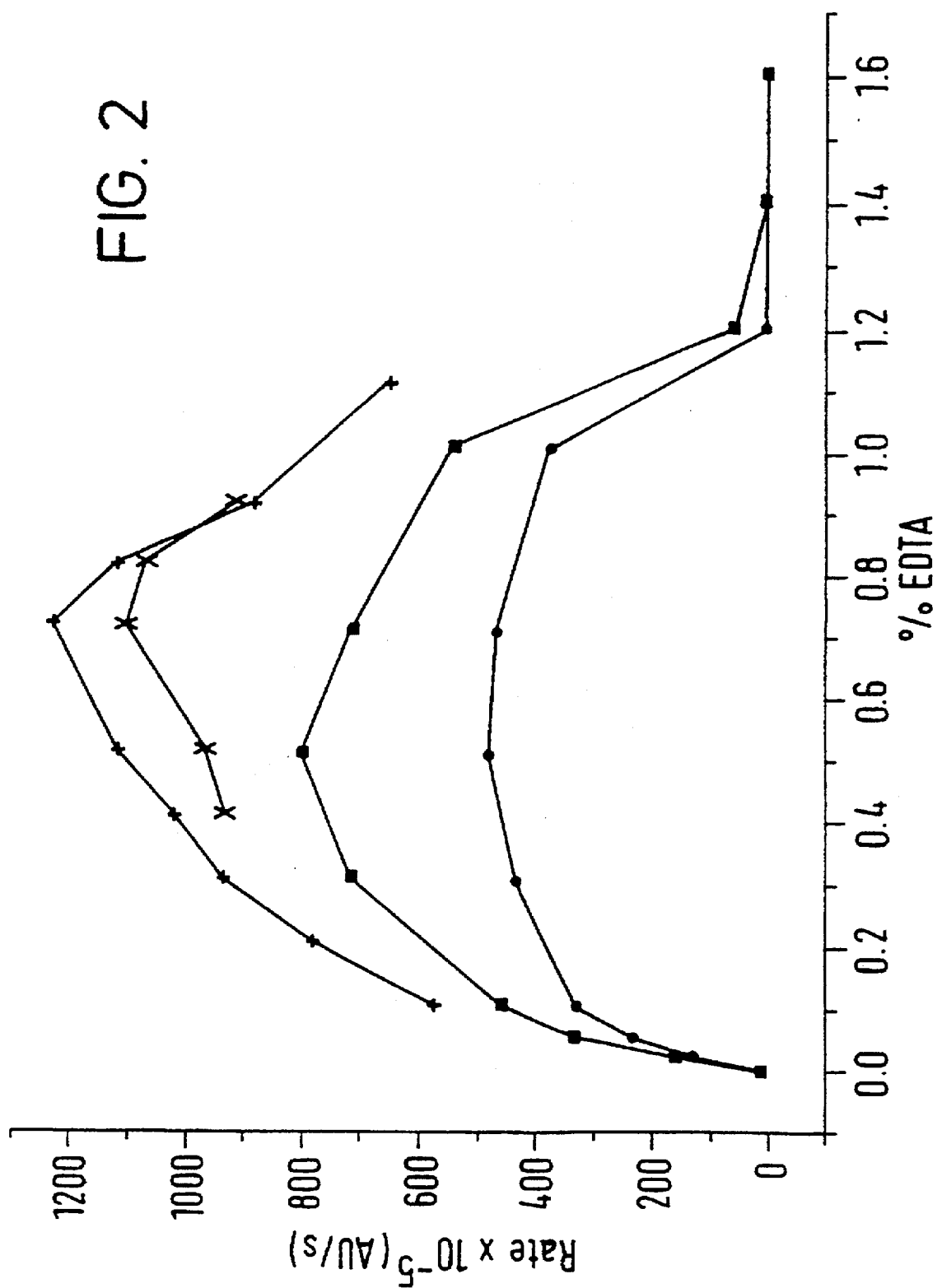

PSEUDOCATALASE ACTIVITY

The present invention relates to a topical composition which is suitable for the treatment of tyrosinase-positive depigmentation disorders and, in particular, treatment of vitiligo. The composition is also suitable for the enhancement of suntanning, particularly the suntanning of fair skin (ie types I and II skins). The composition has improved catalase activity compared to previously known compositions. Methods are also provided for the improvement of the catalase activity of a pseudocatalase composition.

WO-A-92/20354 discloses that vitiligo and other tyrosinase-positive depigmentation disorders can be treated by exposing a patient to UVB light after topical application of a pseudocatalase. A preferred pseudocatalase is manganese (II) bicarbonate complex, prepared by adding manganous chloride to an aqueous solution of sodium bicarbonate, and then mixing the resulting liquid with a hydrophilic cream (100 g of Neribas).

WO-A-92/20321 discloses that suntanning can be enhanced by topical application of a pseudocatalase. The same pseudocatalases are exemplified as in WO-A-92/20354.

Both of these treatments rely upon the in vivo catalytic dismutation of hydrogen peroxide by the pseudocatalase.

It has now been discovered that the said catalytic activity of a pseudocatalase can be increased by the addition of a chelating agent. Particularly suitable chelating agents are EDTA or EDTA analogues and salts thereof.

WO-A-92/20354 and WO-A-92/20321 disclose a composition of manganous chloride (380mg), a solution of sodium bicarbonate (2.3 g) in purified water (3.0 ml), and Neribas (100 g). Neribas is a well-known cream vehicle which contains Macrogol stearate 2000; stearyl alcohol; liquid paraffin; white soft paraffin; polyacrylic acid; sodium hydroxide; disodium EDTA (i.e. ethylenediaminetetraacetic acid disodium salt); methyl and propyl paraben (i.e. 4-hydroxybenzoic acid methyl and propyl esters); and water. The EDTA is present in the cream base for the conventional purposes of removing trace elements which can catalyse autoxidation of oxygen sensitive excipients and boosting the antimicrobial activity of preservatives (eg parabens). There is no suggestion in either of the earlier applications that EDTA improves the catalytic activity of manganese (II) bicarbonate and there was no appreciation at that time that such an effect might exist.

Preferred pseudocatalases disclosed in the Applicant's earlier applications are transition metal bicarbonate complexes. It has now been discovered that the stability of a topical composition comprising a transition metal bicarbonate complex can be improved by storing the composition under carbon dioxide, preferably under pressure in aerosol form. Manganese (II) bicarbonate is thought to be in equilibrium with carbon dioxide, manganese (II) carbonate and water. The presence of carbon dioxide is thought to shift the equilibrium in favour of bicarbonate ions, thereby stabilising them.

According to a first aspect of the present invention, there is provided a topical composition comprising a complex of ions of a transition metal, bicarbonate ions and a chelating agent for chelating the transition metal, provided that, when the composition includes a cream vehicle comprising EDTA, the amount of EDTA is more than 0.1% w/w of the vehicle.

In a second aspect of the invention there is provided a topical composition in aerosol form, comprising a propellant and a complex of ions of a transition metal, bicarbonate ions and a chelating agent for chelating the transition metal.

In a preferred embodiment, the composition additionally comprises a lipid, for example petrolatum, stearyl alcohol, parol, liquid paraffin, white soft paraffin, coconut oil, almond oil, squalene, or any combination thereof.

It is thought that the complex may be partially soluble in the lipid phase, thereby causing the equilibrium between manganese (II) carbonate and manganese (II) bicarbonate to shift towards the latter. This may serve to increase the amount of complex which can be formed so that the activity of composition approaches the theoretical maximum. The presence of a lipid may also aid penetration of the topically applied composition into the skin.

The transition metal is preferably a first-row transition metal, especially manganese, iron or copper, and most preferably manganese.

Whilst not wishing to be constrained by theory, it is thought that a metal with vacant 'd' orbitals is needed, so that a mixed complex of bicarbonate ions and chelating agent can be formed, by donation of electrons from the ligands to the vacant metal 'd' orbitals.

The chelating agent preferably contains two or more carboxylic acid groups or salts thereof.

In a preferred embodiment, the chelating agent is an amino or poly-aminoalkylene polycarboxylic acid, and more preferably a polyamino ($C_2$-$C_3$ alkylene) poly acetic acid such as ethylene diamine tetraacetic acid (EDTA, also known as edetic acid) 1,3-diaminopropane tetraacetic acid (1,3 DPTA), 2-hydroxyethyl ethylenediamine tetraacetic acid (HEDTA), ethylene bis(oxyethylene nitrilo) tetraacetic acid (EGTA), diethylenetriamine pentaacetic acid (DTPA) or triethylene tetraamine hexaacetic acid (TTHA).

In a further preferred embodiment, the chelating agent is a hydroxy polycarboxylic acid, preferably citric acid.

In another preferred embodiment, the chelating agent is a nitrogen-containing heterocyclic compound having a carboxy group on each ring carbon atom adjacent the ring nitrogen atom, preferably 2,6 pyridinedicarboxylic acid (also known as epipicolinic acid).

In another preferred embodiment, the chelating agent is 4-(2-pyridylazo)resorcinol (PAR) or analogues thereof.

Usually, the amount of chelating agent is up to 1.4% by weight of the composition. However, any amount which increases the catalytic activity of the composition can be used.

The composition may additionally comprise calcium ions, since sufferers of depigmentation disorders often also suffer from a calcium deficiency.

In a third aspect, the invention provides a method of preparing a composition as previously described, wherein the chelating agent is added to the ions of the transition metal before adding the bicarbonate ions.

In a fourth aspect, the invention provides the use of a chelating agent to increase the catalytic activity of a pseudocatalase.

Preferably, the pseudocatalase is a transition metal bicarbonate complex. The transition metal and the chelating agent are preferably those described above.

A method is also provided of increasing the catalytic activity of a composition comprising a complex of ions of a transition metal and bicarbonate ions, which method includes the step of incorporating a chelating agent in the composition.

The compositions described above have been found to be effective in a method of pigmenting skin depigmented by a tyrosinase-positive depigmentation disorder, which comprises applying to at least the depigmented areas of the skin an effective amount of the composition as previously described and thereafter exposing the treated skin to UVB light to induce melanin formation in the depigmented areas. In addition, the described compositions are effective in a method of enhancing tanning of skin, which comprises applying to the skin an effective amount of the composition.

The invention is illustrated by the following Examples, and with reference to the accompanying drawings, in which:

BRIEF DESCRIPTION OF THE DRAWINGS

FIG. 2 is similar to FIG. 1 but for different preparations of manganese (II) bicarbonate.

EXAMPLE 1

Figure 1:
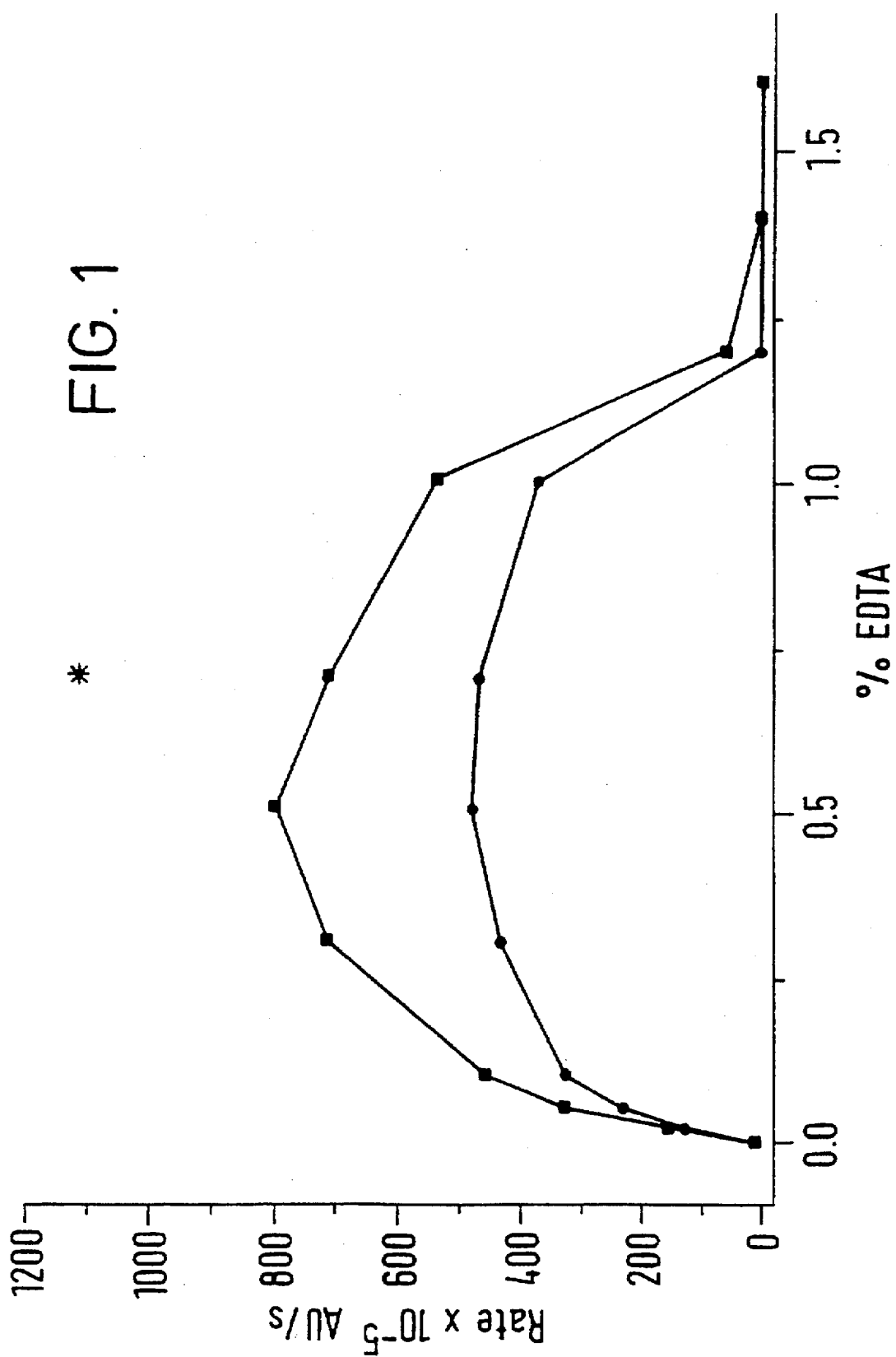
FIG. 1 is a graph demonstrating the effect of the concentration of EDTA on the catalytic activity of manganese (II) bicarbonate.

Sodium bicarbonate (2.3 g) was mixed with an aqueous solution (3 ml) of manganese (II) chloride (10.8% w/w) and calcium chloride (4.0% w/w) and the resultant mixture added to a cream base comprising the following excipients: liquid paraffin; white soft paraffin; Macrogol stearate 2000; stearyl alcohol; polyacrylic acid; EDTA (0.1% by weight of cream base); parabens and sodium hydroxide. The sample (1 g) was added to a solvent (100 ml of 70:30 methanol/water saturated with sodium bicarbonate). The resultant solution was shaken and filtered (0.2 μm), and 2.5 ml filtrate was diluted with 2.5 ml solvent. 1.0 ml of the solution was pipetted into a standard 1cm cuvette, and 1.0 ml of Alizarin B solution (0.2 mg/ml in 50:50 methanol/solvent) was added, followed by 1.0 ml of hydrogen peroxide solution (0.5% by volume in methanol).

The catalytic activity of this sample was then determined by means of measuring the colour change in Alizarin dye (1,2 dihydroxy-anthraquinone) as it is oxidised by hydrogen peroxide. The change in absorbance was monitored at 534 nm, and the rate of reaction was determined from the steepest point on the curve.

Samples of cream base were prepared, each with a different excipient missing. A premix of manganese (II) chloride, calcium chloride and sodium bicarbonate was mixed with each of these samples, and their catalytic activity measured, as described above. The results are shown in Table 1 in activity units (rate per gram of cream).

The results show that the presence of EDTA significantly increases the catalytic activity of the composition. It would also appear that activity is reduced by the removal of lipid components, for example petrolatum, stearyl alcohol and parol.

TABLE 1

| Description | Sample Weight (g) | Initial Abs | Final Abs | Time(s) | Rate | Activity |
| --- | --- | --- | --- | --- | --- | --- |
| Full Formulation | 1.0014 | 1.687 | 1.163 | 120 | 436 | 435 |
| Without Liquid paraffin | 1.0230 | 1.645 | 1.265 | 120 | 316 | 309 |
| Without White soft paraffin | 1.0059 | 1.627 | 1.218 | 120 | 340 | 338 |
| Without Macrogol stearate | 1.0417 | 1.704 | 1.333 | 120 | 309 | 297 |
| Without Stearyl Alcohol | 1.0132 | 1.656 | 1.283 | 120 | 310 | 306 |
| Without Polyacrylic acid/EDTA | 1.0113 | 2.082 | 2.079 | 120 | 2 | 2 |
| Without Polyacrylic acid | 1.0055 | 1.753 | 1.266 | 120 | 405 | 403 |
| Without EDTA | 1.0045 | 2.068 | 2.059 | 120 | 7 | 7 |
| Without Parabens | 1.0078 | 1.701 | 1.343 | 120 | 298 | 296 |
| Without NaOH (Trisamino used) | 1.0192 | 1.784 | 1.296 | 120 | 406 | 398 |
| Full Formulation (0.7% EDTA) | 1.0003 | 2.088 | 1.578 | 120 | 425 | 425 |
| Liquid Crystal Formulation (0.1% EDTA) | 1.0111 | 1.695 | 1.231 | 120 | 386 | 382 |
| Liquid Crystal Formulation (0.7% EDTA) | 1.0249 | 2.056 | 1.479 | 120 | 480 | 468 |
| Mn/Ca bicarbonate Aq* | 1.0078 | 2.062 | 2.057 | 120 | 4 | 4 |
| Mn/Ca bicarbonate Aq EDTA** | 1.0078 | 1.945 | 1.829 | 120 | 96 | 95 |

*Manganese chloride/calcium chloride solution and Sodium bicarbonate plus 100 ml water - analysed as per cream samples
**Manganese chloride/calcium chloride solution and Sodium bicarbonate plus 100 ml 0.1% EDTA (aq) analysed as per cream samples

EXAMPLE 2

Further investigations were performed to investigate the connection between amounts of EDTA and catalytic activity. Cream bases were prepared as in Example 1 with various concentrations of EDTA up to a maximum of 1.6% by weight. Manganese chloride (380 mg) was added to a solution of sodium bicarbonate (2.3 g) and calcium chloride (4.0% w/w) in purified water (3.0 ml) at ambient temperature. The mixture was allowed to stand until the evolution of gas had ceased. The resultant pinkish brown liquid was mixed with the various cream base preparations. The catalytic activity of these preparations was then measured as described in Example 1, and the results are shown as "■" in FIG. 1.

Candidate aerosol formulations of the various cream bases were also prepared. The activity of these formulations is shown as "●" in FIG. 1.

It can be seen that the maximum activity is obtained at about 0.5% by weight of EDTA in both the aerosol and the non-aerosol formulations. More than 0.5% by weight of EDTA appears to reduce the catalytic activity of preparations. The aerosol formulation exhibits less activity than the non-aerosol formulation, because there is less pseudocatalase cream base present.

EXAMPLE 3

A formulation was prepared as in Example 1 except that the EDTA (solid) was added first to an aqueous solution of manganese (II) chloride (10.8% w/w) and calcium chloride (4.0% w/w) and then sodium bicarbonate (solid, 2.3 g) was added. No precipitate of manganese carbonate ensued on addition of the bicarbonate. The activity of a sample prepared from this formulation (0.7% EDTA) was tested as in Example 1, and this is shown as "*" in FIG. 1.

It can be seen that the activity is significantly higher than the other formulations, and it is postulated that this is a consequence of a higher EDTA/$Mn^{2+}$ complex concentration.

It has been observed that the addition of bicarbonate to manganese chloride in water leads to the precipitation of a white solid, mostly composed of manganese carbonate. It is thought that some manganese carbonate remains as solid when the cream base is added, so that some manganese ions are unavailable for chelation with the EDTA. This may explain the higher activity of the composition of Example 3, since all of the manganese ions are available for chelation.

EXAMPLE 4

It is thought that the level of EDTA which should theoretically give an optimum catalytic activity is that which corresponds to a 1:1 stoichiometric ratio of EDTA to manganese ions (which is 0.7% by weight of EDTA). In fact, the results of Example 2 demonstrate that the empirical amount of EDTA which results in optimum activity is 0.5% by weight of composition.

Various EDTA/Mn bicarbonate formulations were prepared as in Example 3, with varying concentrations of EDTA (0.1% to 1.1% by weight), and the activities of these formulations were tested. The results are shown in FIG. 2 as "+". The exercise was repeated (shown as "×" in FIG. 2). It can be seen that the catalytic activity of these formulations is significantly higher than the earlier prepared formulations of Example 2. Moreover optimum activity is shown by the formulation containing 0.7% EDTA, as is theoretically predicted.

EXAMPLE 5

Various formulations were prepared as in Example 1 with various different chelating agents instead of EDTA, in an amount equivalent to a 1:1 molar ratio of chelating agent to manganese chloride. The activity of these formulations was compared with the activity of a control sample having no chelating agent. The results are shown below in Table 2.

It can be seen that a significantly increased activity is shown by formulations containing an EDTA analogue, citric acid, or 2,6 pyridinedicarboxylic acid. In addition, a high activity is shown if 4-(2-pyridylazo) resorcinol (PAR) is used as a chelating agent.

Formulations as described above with increased catalytic activity can be used to treat depigmentation disorders such as vitiligo as described in WO-A-92/20354. They can also be used as suntanning enhancement compositions as described in WO-A-92/20231. It is not intended however that the uses of the novel compositions described herein should be limited in any way.

TABLE 2

| Chelating Agent | | Activity | Profile 1 control = 1.0 | Profile 2 EDTA = 1.0 |
|---|---|---|---|---|
| EDTA Analogues | | | | |
| Ethylenediamine tetraacetic acid (2 Na aalt) | EDTA (2Na) | 236 | 11.8 | 1.0 |
| Ethylenediamine tetraacetic acid (4 Na salt) | EDTA (4Na) | 229 | 11.5 | 1.0 |
| 1,3-Diaminopropane tetraacetic acid | 1,3 DPTA | 145 | 7.3 | 0.6 |
| 1,2-Diaminopropane tetraacetic acid | 1,2 DPTA | 66 | 3.3 | 0.3 |
| 2-Hydroxyethyl ethylenediamine triacetic acid (3 Na salt) | HEDTA | 302 | 15.1 | 1.3 |
| Ethylene bis(oxyethylene nitrilo) | EGTA | 410 | 20.5 | 1.7 |
| Diethylenetriamine pentaacetic acid | DTPA | 242 | 12.1 | 1.0 |
| Triethylenetetraamine hexaacetic acid | TTHA | 301 | 15.1 | 1.3 |
| 1,2-Diaminocyclohexane tetraacetic acid | DCTA | 24 | 1.2 | 0.1 |
| Diaminohexane tetraacetic acid | DHTA | 8 | 0.4 | 0.0 |
| Ethylenediamine tetrapropionic acid (4 Na aalt) | EDTPA | 26 | 1.3 | 0.1 |
| Others | | | | |
| Hexacyclen trisulphate | | 26 | 1.3 | 0.1 |
| Dibenzo 18-Crown-6 | | 33 | 1.7 | 0.1 |
| Dibenzo 24-Crown-8 | | 26 | 1.3 | 0.1 |
| 18-Crown-6 | | 25 | 1.3 | 0.1 |
| 15-Crown-5 | | 27 | 1.4 | 0.1 |
| Tetraazocyclotetradecane tetraacetic acid (4 HCl.4$H_2O$) | TACTTA | 7 | 0.4 | 0.0 |
| Hexaoxa diazabicyclohexacoeane | HODCH | 26 | 1.3 | 0.1 |
| Hexathiacyclooctadecane | HTCD | 36 | 1.8 | 0.2 |
| 8-Hydroxyquinoline-5-sulphonic acid monohydrate | | 59 | 3.0 | 0.2 |
| Pyrrolidine carbodithio acid, ammonium salt | | 22 | 1.1 | 0.1 |
| 1-(2-Pyridylazo)-2-naphthol | PAN | 31 | 1.6 | 0.1 |
| 4-(2-Pyridylazo)resorcinol | PAR | 709 | 35.5 | 3.0 |
| Ascorbic acid | | | | 0.01 |
| Oxalic acid | | | | 0.01 |
| Salicylic acid | | | | 0.01 |
| Citric acid | | | | 1.25 |
| Tartaric acid | | | | 0.01 |
| DL leucine | | | | 0.01 |
| 2,6-Pyridinedicarboxylic acid | | | | 2.00 |
| 4-(4-nitrophenylazo)resorcinol | | | | 0.01 |
| Dithizone | | | | 0.02 |
| 1,10-phenanthroline | | | | 0.04 |
| Manganese Complexes | | | | |
| Manganeae phthalocyanine | | 58 | 2.9 | 0.2 |
| Manganese diethylenetriamine pentaacetic acid (3 H salt) $H_2O$ | MnDTPA | 42 | 2.1 | 0.2 |

TABLE 2-continued

| Chelating Agent | Activity | Profile 1 control = 1.0 | Profile 2 EDTA = 1.0 |
|---|---|---|---|
| Control | | | |
| No complexing agent | 20 | 1.0 | 0.1 |

We claim:

1. A topical composition comprising a complex of ions of a transition metal, bicarbonate ions and a chelating agent for chelating the transition metal and for increasing pseudocatalase activity, such that, when the chelating agent is ethylenediaminetetraacetic acid, the amount of the ethylenediaminetetraacetic acid in a topical composition comprising a cream vehicle is more than 0.1% w/w and ranges up to 1.6% w/w of the cream vehicle.

2. A composition as claimed in claim 1, which is stored under carbon dioxide.

3. A topical composition as claimed in claim 1 in aerosol form comprising a propellant.

4. A composition as claimed in claim 3, wherein the propellant is carbon dioxide.

5. A composition as claimed in claim 1, additionally comprising a lipid.

6. A composition as claimed in claim 1, wherein the transition metal is manganese, iron or copper.

7. A composition as claimed in claim 6, wherein the transition metal is manganese.

8. A composition as claimed in claim 1, wherein the amount of the chelating agent is up to 1.4% by weight of the composition.

9. A composition as claimed in claim 1, wherein the stoichiometric ratio of the chelating agent to the ions of the transition metal is about 1:1.

10. A composition as claimed in claim 1, wherein the chelating agent contains two or more carboxylic acid groups or salts thereof.

11. A composition as claimed in claim 1, wherein the chelating agent is selected from the group consisting of amino or polyamino alkylene polycarboxylic acids, hydroxy polycarboxylic acids, nitrogen-containing heterocyclic compounds having a carboxy group on each ring carbon atom adjacent the ring nitrogen atom, and salts thereof.

12. A composition as claimed in claim 11, wherein the chelating agent is a polyamino ($C_2$–$C_3$ alkylene) poly acetic acid or salt thereof.

13. A composition as claimed in claim 12, wherein the chelating agent is ethylene diamine tetraacetic acid (EDTA), 1,3-diaminopropane tetraacetic acid (1,3 DTPA), 2-hydroxyethyl ethylenediamine tetraacetic acid (HEDTA), ethylene bis(oxyethylene nitrile) tetraacetic acid (EGTA), diethylenetriamine pentaacetic acid (DTPA) or triethylene tetraamine hexaacetic acid (TTHA).

14. A composition as claimed in claim 11, wherein the chelating agent is citric acid or 2,6-pyridine dicarboxylic acid.

15. A composition as claimed in claim 1, wherein the chelating agent is 4-(2-pyridylazo)resorcinol (PAR).

16. A method of preparing a composition as claimed in claim 1, wherein the chelating agent is added to the ions of the transition metal before adding the bicarbonate ions.

17. A method of increasing the pseudocatalase activity of a composition comprising a complex of ions of a transition metal and bicarbonate ions, which method includes the step of incorporating an effective amount of a chelating agent in the composition.

18. A method as claimed in claim 17, wherein the chelating agent is selected from the group consisting of amino or polyamino alkylene polycarboxylic acids, hydroxy polycarboxylic acids, nitrogen-containing heterocyclic compounds having a carboxy group on each ring carbon atom adjacent the ring nitrogen atom, and salts thereof.

19. A method of pigmenting skin depigmented by a tyrosinase-positive depigmentation disorder which comprises applying to at least the depigmented areas of the skin an effective amount of a composition as claimed in claim 1 and thereafter exposing the treated skin to UVB light to induce melanin formation in the depigmented areas.

20. A method of enhancing tanning of skin which comprises applying to the skin an effective amount of a composition as claimed in claim 1.

* * * * *